United States Patent
Sgro

Patent Number: 6,113,623
Date of Patent: Sep. 5, 2000

[54] PROSTHETIC DEVICE AND METHOD FOR EVENTRATION REPAIR

[75] Inventor: Jean Claude Sgro, Dijon, France

[73] Assignee: Cabinet Beau de Lomenie, Paris, France

[21] Appl. No.: 09/001,954

[22] Filed: Dec. 31, 1997

Related U.S. Application Data

[63] Continuation-in-part of application No. 08/600,308, Feb. 12, 1996, abandoned, which is a continuation of application No. 08/230,479, Apr. 20, 1994, abandoned.

[51] Int. Cl.⁷ .................................................. A61B 17/04
[52] U.S. Cl. ........................... 606/215; 606/151; 623/11
[58] Field of Search ........................ 623/11, 14; 128/898; 606/151, 213, 214, 215

[56] References Cited

U.S. PATENT DOCUMENTS

| | | | |
|---|---|---|---|
| 5,116,357 | 5/1992 | Eberbach | 606/213 |
| 5,254,133 | 10/1993 | Seid | 606/215 |
| 5,405,360 | 4/1995 | Tovey | 606/151 |
| 5,741,297 | 4/1998 | Simon | 606/151 |
| 5,743,917 | 4/1998 | Saxon | 623/11 |

*Primary Examiner*—Bruce E. Snow
*Attorney, Agent, or Firm*—Harris Beach & Wilcox, LLP

[57] ABSTRACT

A fabric prosthetic unit for repairing an incissional hernia including a joining strip is intended to be positioned in a space created by a tear or collapse of an aponeurosis. Two substantially planer sheets of colonisable flexible prosthetic fabric material extend substantially parallel to each other and are linked together by the joining strip. Each of the planer sheets includes flap extensions lying opposite to each other and are on either side of an edge part of a corresponding face on the joining strip.

12 Claims, 5 Drawing Sheets

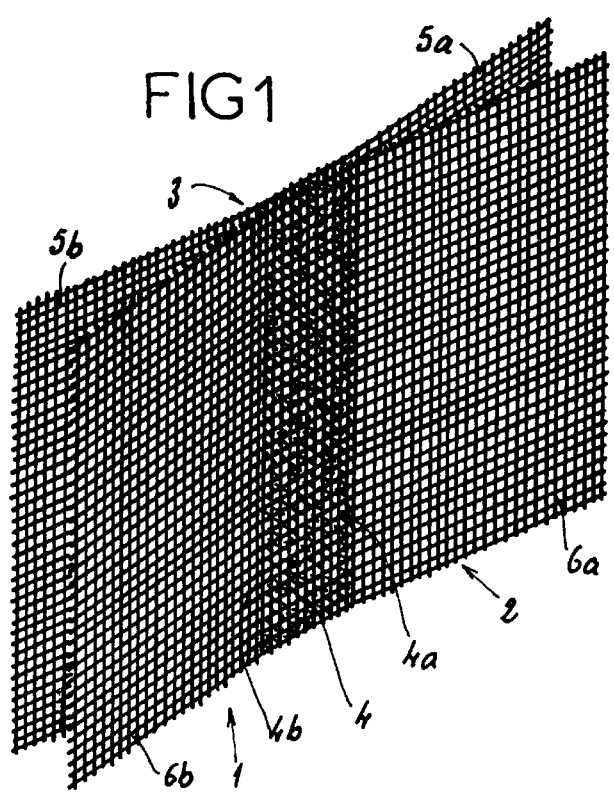
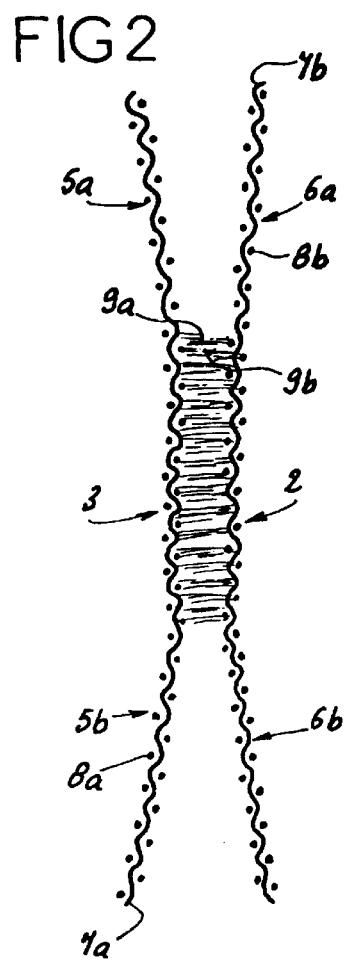
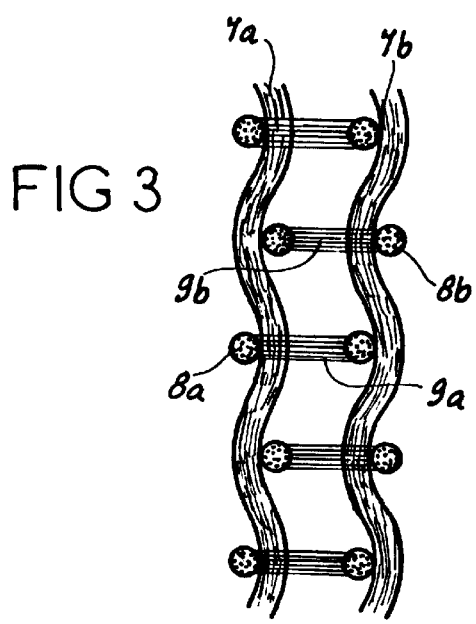

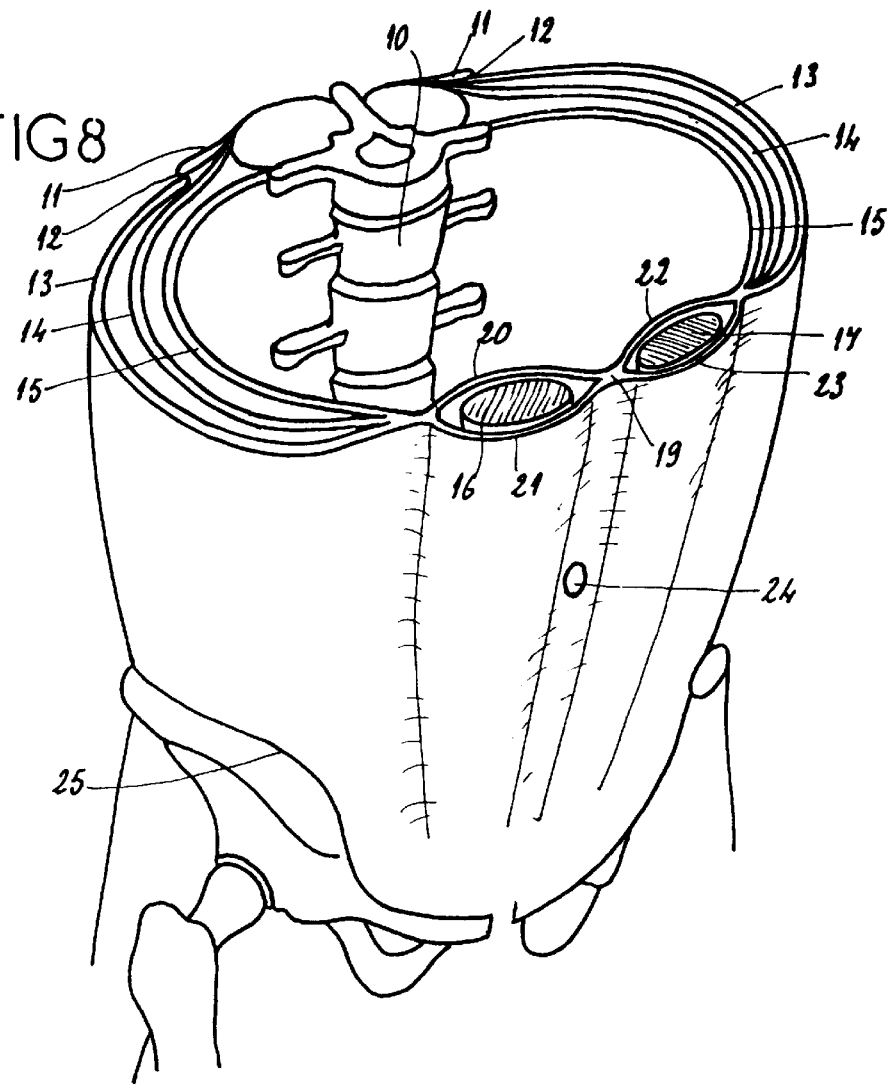
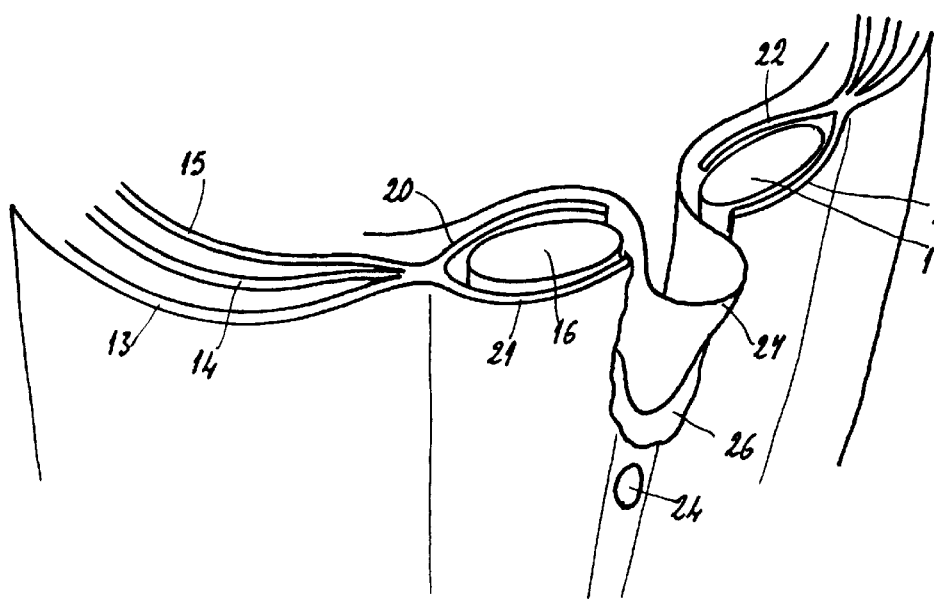

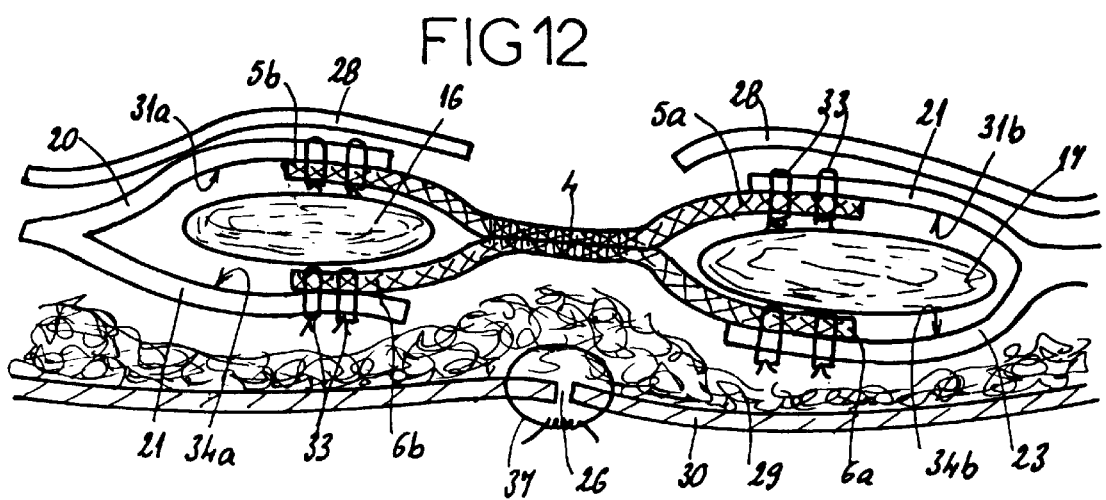

PROSTHETIC DEVICE AND METHOD FOR EVENTRATION REPAIR

RELATED APPLICATION

This is a Continuation-in-Part application of Ser. No. 08/600,308 filed Feb. 12, 1996, now abandoned which is a contination of originally filed application Ser. No. 08/230,479 filed on Apr. 20, 1994, now abandoned claiming priority from French application N°9305185, filed on Apr. 23, 1993.

BACKGROUND OF THE INVENTION

The invention relates to the technical sector of abdominal wall reinforcements or replacements, by extension addressing cases of muscle and aponeurosis loss.

More particularly, the invention concerns a prosthesis or prosthetic element for the treatment of vertical abdominal eventrations, and preferably median eventrations.

A vertical eventration or vertical median eventration occurs or can occur when the aponeuroses surrounding the rectus abdominis muscles are torn, for example, by trauma or failed suturing after open abdominal surgery, or when the muscular system spontaneously collapses. The internal pushing pressure generated by the intestines on the abdominal muscle wall is so great that the space created by the tear between the rectus muscles becomes filled with intestines enveloped in the peritoneum which spills outside the body.

U.S. Pat. No. 4,769,038 discloses a three-layered prosthesis with two opening sheets fastened to a third. The prosthesis, therefore, has the general appearance of a letter Y, rendering it unsuitable for the treatment of eventration.

Other prosthetic devices for body wall repair are known and described in patent WO 92/19162. The prosthetic device is shaped like a mushroom with a central cylinder fastened to two flat parts by a VELCRO-type system. This prosthetic unit is a plug preventing the orifice from skining over. Such a component is unsuitable for the treatment of vertical abdominal eventrations.

U.S. Pat. No. 5,254,133 to Seid discloses a prosthetic device for hernial repair, and in particular inguinal hernia repair. This type of device is commonly called a plug patch, and comprises two planar sheets of material or patches linked together by an elongated locating segment. The device can be folded or rolled up for insertion into a laparoscope and subsequently unrolled or unfolded at the site of the hernia.

The elongated locating segment makes this device, and hernial plug devices in general, unsuitable for the repair of eventrations because the extended length of the elongated locating segment between the two planar sheets prevents the muscles which have been separated by the eventration from being brought towards each other, the latter being a necessary condition for adequate eventration repair and for preventing a recurrence thereof.

Other plug devices are also known from U.S. Pat. 5,116,357 to Eberbach, and U.S. Pat. No. 5,147,374 to Fernandez. None of the prosthetic devices described in these patents is suitable for use in eventration repair, essentially for the reasons given above.

Accordingly, the purpose of the prosthetic device of this invention, principally designed for various types of eventration, is to reinforce the muscle wall tissue at the implant site, improving implant integration into the tissue while combining strength and resistance to deformation with great flexibility. In particular, the structure of the prosthetic device according to the invention is such that it enables a redistribution or resolution of abdominal pushing or thrust forces over a wide area. This capability reduces the risk of tearing of the device at the attachment sites of the prosthesis, and a slipping of the device leading to a recurrence of the eventration. Such a problem currently exists for the traditionally used single sheet of prosthetic material in eventration repair.

Another object of the invention is to provide a prosthetic device for repairing a torn aponeurosis between a first and second muscles.

It is a further object of the invention to provide a prosthetic device for eventration repair having a structure that enables a redistribution or resolution of abdominal pushing or thrust forces over a wide area.

A further object of the invention is to provide a prosthetic device for vertical median eventration repair which recreates a resistant and flexible prosthetic aponeurosis between the abdominis rectus muscles, and substantially recreates the linea alba.

Still yet another object of the invention is to provide a method of eventration repair using the prosthetic device according to the invention.

As stated previously, in order to enable a correct resolution of the abdominal pushing forces or thrust generated by the intestines, it is necessary to bring the rectus muscles and their aponeuroses towards each other. The applicant of present invention has solved this problem by providing a prosthetic device which enables excellent force distribution while at the same time providing a resistant repair zone to fill the space caused by the eventration and reconstitute the linea alba.

DESCRIPTION OF TERMS

In the following description the following terms have the following meanings:

"aponeurosis" is any membrane constituted by dense conjunctive fibres surrounding a muscle, and which serves as an insertion means for a flat muscle, or which forms a separation between certain muscular planes or fascia;

"internal organ" is an individualized part of the body intended to fulfil a determined function and contained within the peritoneum, for example the intestines;

"pushing movement or "pushing force" or "thrust" is a pressure, movement or force exerted by the presence of an internal organ as previously defined towards the exterior of the body.

SUMMARY OF THE INVENTION

To achieve these objectives, a prosthetic device was conceived and developed as substantially-claimed and represented in the drawings.

In particular, for repairing an eventration resulting from a tear in or a collapse of an aponeurosis linking a first and second muscles having an anterior and posterior faces, and from a pushing movement of an internal organ or part thereof into an anatomic space created by said tear or collapse, the device comprises:

a three-dimensionally substantially void but structured joining strip intended to be positioned in said anatomic space without plugging it, a first and second substantially planar sheets of a colonisable flexible prosthetic fabric material extending substantially parallel to each other, and linked together by said joining strip, thus forming two opposite faces respectively common to said first and second planar sheets, each of said planar sheets comprising flap extensions lying opposite to each other and either side of an edge part of a corresponding face of said joining strip, for positioning in proximity to a same anterior or posterior face of said first and second muscles respectively, whereby the first and second planar sheets are placed in proximity to said anterior and posterior faces respectively of the two muscles, and the joining strip resolves thrust or forces generated by said pushing movement in a position formerly occupied by the torn aponeurosis in the anatomic space.

Preferably, the first and second muscles are the left and right rectus abdominis muscles, and the aponeurosis is the linea alba.

Advantageously, the three-dimensionally structured joining strip has a thickness comprised between about 0.7 mm to about 6 mm.

In a more preferred embodiment of the present invention, the three-dimensionally structured joining strip is cut away between said sheets. Even more preferably, the joining strip is cut away at a point where the strip meets the edges of the substantially planar sheets. The joining strip preferably has a length comprised from between about 10 cm to about 70 cm.

According to another preferred embodiment, the three-dimensionally structured joining strip is a knitted structure formed by knitting a part of each prosthetic fabric material sheet together. In this case, the three-dimensionally structured joining strip is preferably a knitted structure formed by knitting filaments, preferably weft filaments, from a first sheet of prosthetic fabric material with filaments, preferably weft filaments, from a second sheet of fabric prosthetic material.

In an alternative preferred embodiment, the three-dimensionally structured joining strip is a woven structure formed by weaving a part of each prosthetic fabric material sheet together. In this case, the three-dimensionally structured joining strip is preferably a woven structure formed by weaving filaments, preferably weft filaments, from a first sheet of prosthetic fabric material with filaments, preferably weft filaments, from a second sheet of fabric prosthetic material.

In a further preferred embodiment, the flexible prosthetic fabric material sheets are made fray resistant fibres or filaments and more preferably from fray resistant knitted polyester fibres.

The prosthetic device is also preferably impregnated with collagen, and preferably collagen selected to favor penetration of connective tissue cells for improved integration.

According to another object of the invention, the method of repairing an eventration, resulting from a tear in or a collapse of an aponeurosis linking a first and second muscles having an anterior and posterior faces, and from a pushing movement or thrust of an internal organ or part thereof into an anatomic space created by said tear or collapse, comprises the following steps:

applying to the eventration a prosthetic device comprising a three-dimensionally substantially void but structured joining strip, a first and second substantially planar sheets of a colonisable flexible prosthetic fabric material extending substantially parallel to each other, and linked together by said joining strip, thus forming two opposite faces respectively common to said first and second planar sheets, each of said planar sheets comprising flap extensions lying opposite to each other and either side of an edge part of a corresponding face of said joining strip, placing and attaching the flaps of said first substantially planar sheet of said prosthetic device in proximity to the posterior face of the two muscles, placing the joining strip of said prosthetic device in a position formerly occupied by the torn aponeurosis in the anatomic space, placing and attaching the flaps of said second substantially planar sheet of said prosthetic device in proximity to the anterior face of said muscles, whereby the joining strip of said prosthetic device resolves thrust or forces generated by said pushing movement and recreates said torn aponeurosis.

Preferably, the device is preshaped to a size corresponding to the eventration to be repaired before application.

Even more preferably, the preshaping of the device comprises cutting the sheets of the device to the required size and separating, by cutting away, a part of said joining strip at the edges of said sheets.

In a preferred embodiment of the method of the invention, the flaps are placed and attached directly to a same face of the two muscles.

In another preferred embodiment of the method of the invention, the joining strip of the prosthetic device is attached directly to a same face of the two muscles by suture clips which are themselves attached and interconnected by an annular thread.

BRIEF DESCRIPTION OF THE DRAWINGS

The invention is explained in greater detail hereinafter reference being made to the accompanying drawings, in which:

FIG. 1 is an elevated perspective view of the preferred embodiment of the prosthetic device according to the present invention.

FIG. 2 is a schematic plan view of the prosthetic device FIG. 1.

FIG. 3 is a close-up view on an enlarged scale of the central three-dimensional zone of the prosthetic device according to the preferred embodiment of the invention.

FIG. 8 is an elevated perspective schematic view of a cross-section of the human body through the abdominal area showing different anatomical structures.

FIG. 9 is a close-up view on an enlarged scale of the same abdominal area illustrated in FIG. 8, showing schematically the presence of a vertical abdominal eventration.

FIG. 12 is a view taken across the abdominal wall area showing the position of a prosthetic device similar to FIG. 11.

DETAILED DESCRIPTION OF THE INVENTION

Figure 4:
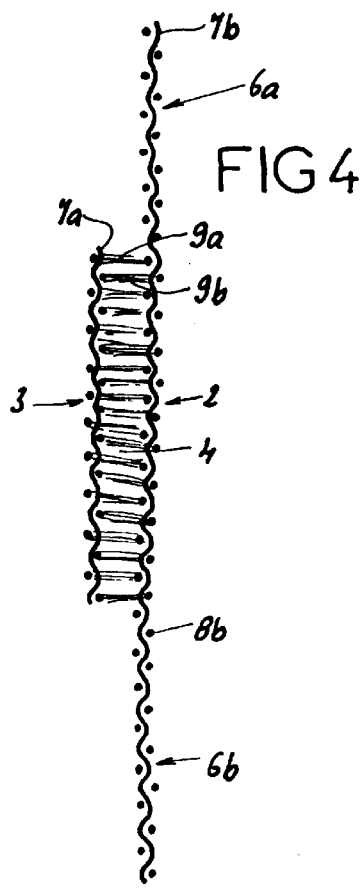
FIG. 4 is a schematic plan view of an alternative embodiment of the prosthetic device according to the present invention.

The prosthetic device of the invention is illustrated generally in FIG. 1 by the reference (1). The device (1) comprises two substantially planar sheets (2, 3) of a flexible prosthetic fabric material which extend in parallel to each other, thus forming two opposite faces respectively common to said first and second planar sheets. Each of said planar sheets comprises flap extensions (5a, 5b, 6a, 6b) lying opposite to each other and either side of an edge part (4a, 4b) of a corresponding face of a joining strip, which will be described in more detail hereafter, for positioning in proximity to a same anterior or posterior face of a first and second muscles respectively.

The sheets (2, 3) are preferably generally rectangular in shape, although they may be made or cut to any suitable shape by the manufacturer or the surgeon. The flexible prosthetic fabric material is preferably biocompatible and can be chosen from those known to the skilled person, such as for example, polyester, nylon, polypropylene and the like. The sheets (2, 3) are preferably in the form of a knitted or woven mesh of knitted polyester fibres, but are not limited thereto. The choice of knitted polyester fibres enables the sheets (2, 3) to withstand the forces exerted on the prosthetic device (1) in use whilst at the same time remaining biocompatible and enabling or enhancing colonisation by native cells.

As mentioned above, the two sheets (2, 3) are linked to each other by a three-dimensionally substantially void but structured joining strip (4), the details of which we will be given below. Each sheet (2, 3) is thus substantially divided into two flexible flaps (5a, 5b, 6a, 6b) either side of said strip (4).

As will be evident from FIG. 1, the three-dimensionally substantially void but structured joining strip (4) is relatively narrow. However, in general, the strip (4) measures approximately between about 6 mm to about 30 mm in the lengthwise direction of the sheets (2, 3) and has a thickness comprised between about 0.7 mm to about 6 mm. The strip is substantially void in order for it to be relatively resistant whilst at the same time remaining relatively light and flexible.

The length of the three-dimensionally structured joining strip (4) generally coincides with one of the dimensions of the sheets (2, 3), and is preferably from between about 10 cm to about 70 cm in length. However, it should be realized that it is also possible for the strip (4) to link the sheets (2, 3) across only a part thereof. The strip could, for example, extend from a point at a predetermined distance inside the outer edge of one side of the sheets (2, 3) to a point at a predetermined distance inside the outer edge of the other side of said sheets (2, 3). In a particularly preferred embodiment, the joining strip (4) is cut away between the sheets (2,3) at the edges thereof, so that the sheets extend beyond said strip. This enables the device to be attached centrally, and more easily, for example by direct attachment to the muscles.

Preferably, the joining strip (4) is formed by knitting or weaving a part of each prosthetic fabric material sheet (2, 3) together. In the preferred embodiments of the invention the joining strip (4) is preferably a knitted or woven structure formed by knitting or weaving filaments, preferably weft filaments, from a first sheet (2) of prosthetic fabric material with filaments, preferably weft filaments, from a second sheet (3) of fabric prosthetic material. Preferably, the strip is formed by rib knitting. FIG. 2 shows schematically a top plan view of FIG. 1, wherein the four flaps (5a, 5b, 6a, 6b) of the prosthetic fabric sheets (2, 3) are indicated. The sheets (2, 3) are comprised of chain filaments or fibres (7a, 7b) which run along the length (L) of the sheets, and weft filaments or fibres (8a, 8b) running in a transverse direction over and under the chain fibres or filaments (7a, 7b). Only one chain filament or fibre is shown on each sheet (2, 3) for reasons of clarity.

As is shown more clearly in FIG. 3, The strip (4) is formed by knitting or weaving the weft filaments or fibres (8a) on one sheet (3) with corresponding weft filaments or fibres (8b) of the other sheet (2), and vice-versa in alternating fashion, such that a three dimensional cross-linked structure (9a, 9b) is formed by some of the filaments or fibres (8a, 8b) of each sheet (2, 3) between said two sheets (2, 3).

Figure 5:
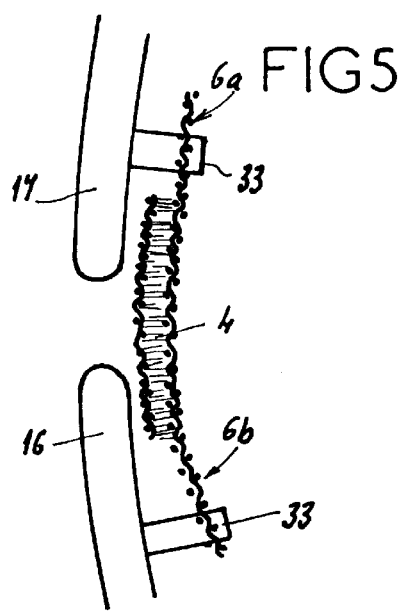
FIG. 5 is a schematic plan view of the application of the alternative embodiment of FIG. 4 to two muscles.

An alternative embodiment of the device of the present invention is illustrated by FIG. 4. In this figure, one of the sheets (3) has been partially cut away to leave the joining strip (4) free on one face. FIG. 5 illustrates the application of such a prosthetic device directly to the same face of two muscles, for example the right (16) and left (17) rectus abdominis muscles via at least one staple or suture (33) which attaches a flap (6a) so that the joining strip (4) is positioned in the anatomic space between the two muscles.

Figure 6:
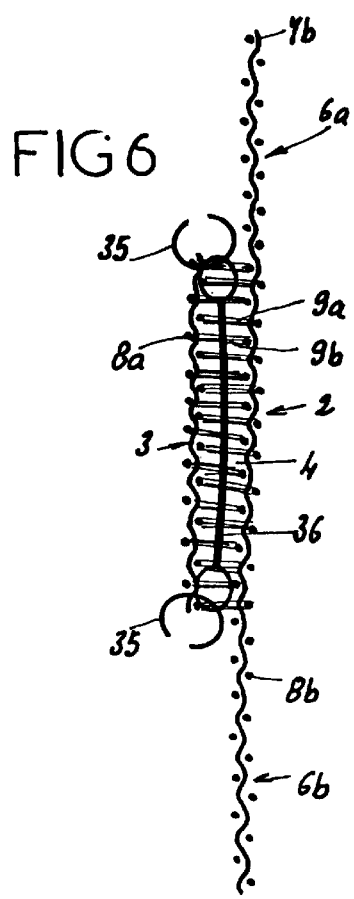
FIG. 6 is a schematic plan view of an alternative embodiment of the prosthetic device according to FIG. 4 and 5.
Figure 7:
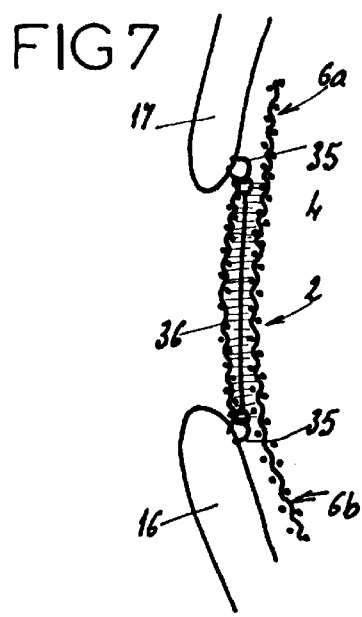
FIG. 7 is a schematic plan view of the application of the alternative embodiment of FIG. 6 to two muscles.

FIGS. 6 and 7 show an alternative embodiment of the device of FIGS. 4 and 5, wherein the device is attached directly to the same face of two muscles by suture clips (35) which are themselves connected to a thread (36) threaded through the joining strip (4).

A more detailed description of the relevant anatomy involved, the positioning of the device, and method of repair will become clearer from the following non-limiting description, which will detail the application of prosthetic device essentially according to FIG. 1 as described above for treating a vertical median eventration:

FIG. 8 is a schematic elevated perspective view of a cross-section of the human body through the abdominal area showing the major anatomical structures in their substantially normal state. The layers of subcutaneous and cutaneous tissue have been removed for clarity. The figure shows the spinal column (10), the lumbar aponeurosis (11), the latissimus (12), the external oblique muscle (13), the internal oblique muscle (14), and the transversus muscle (15). Towards the front of the figure are the right (16) and left (17) rectus abdominis muscles divided by an aponeurosis known as the linea alba (19), which is generally a solid structure composed of enravelled or enmeshed fibres extending from the sheaths surrounding the rectus abdominis muscles. These muscles (16, 17) are surrounded by the right posterior (20) and anterior (21) rectus sheaths, and the left posterior (22) and anterior (23) rectus sheaths. Also illustrated are the umbilicus (24) and the superior iliac spine (25).

When a patient suffering from a vertical median eventration is brought in for treatment, the anatomical situation is similar to that illustrated schematically in FIG. 9. In this figure, it can be seen that a tear (26) has formed in the linea alba (19), and the peritoneum (27) has been pushed out towards the exterior of the body by the pushing movement or forces generated by the organs held within, which in this particular case is often the intestines (not shown).

Figure 10:
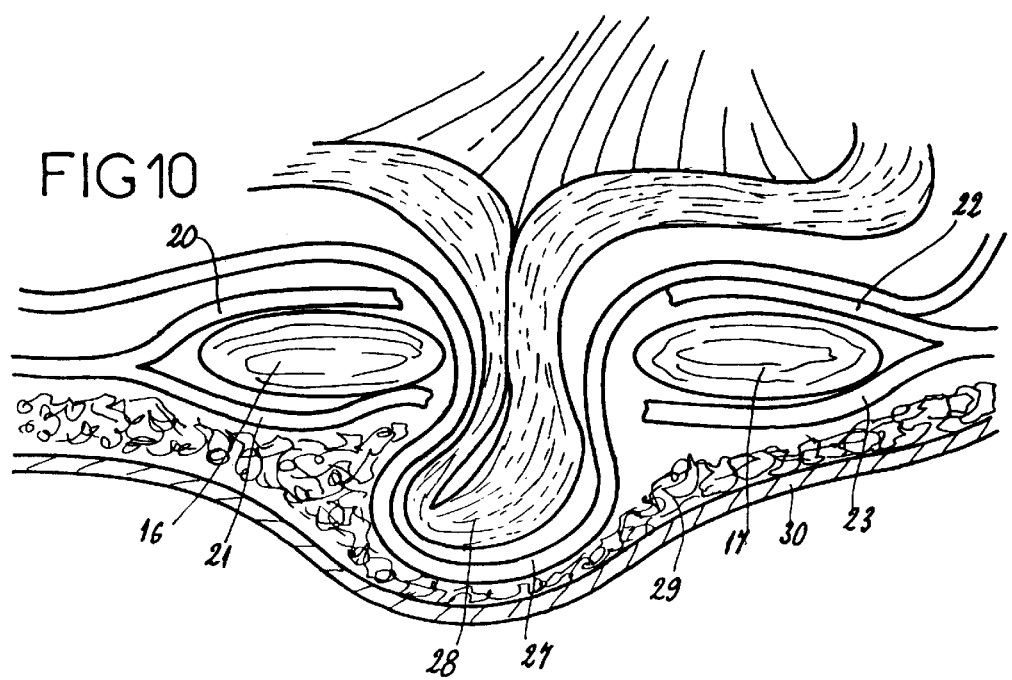
FIG. 10 is a view taken across the abdominal wall area showing the same vertical eventration as in FIG. 9 and its position in relation to the other abdominal structures.

An equivalent view is illustrated by FIG. 10, which is a cross-sectional view of the abdominal wall area showing the same vertical eventration, and also illustrating a trapped intestinal loop (28), and the layers of subcutaneous (29) and cutaneous (30) tissue.

Figure 11:
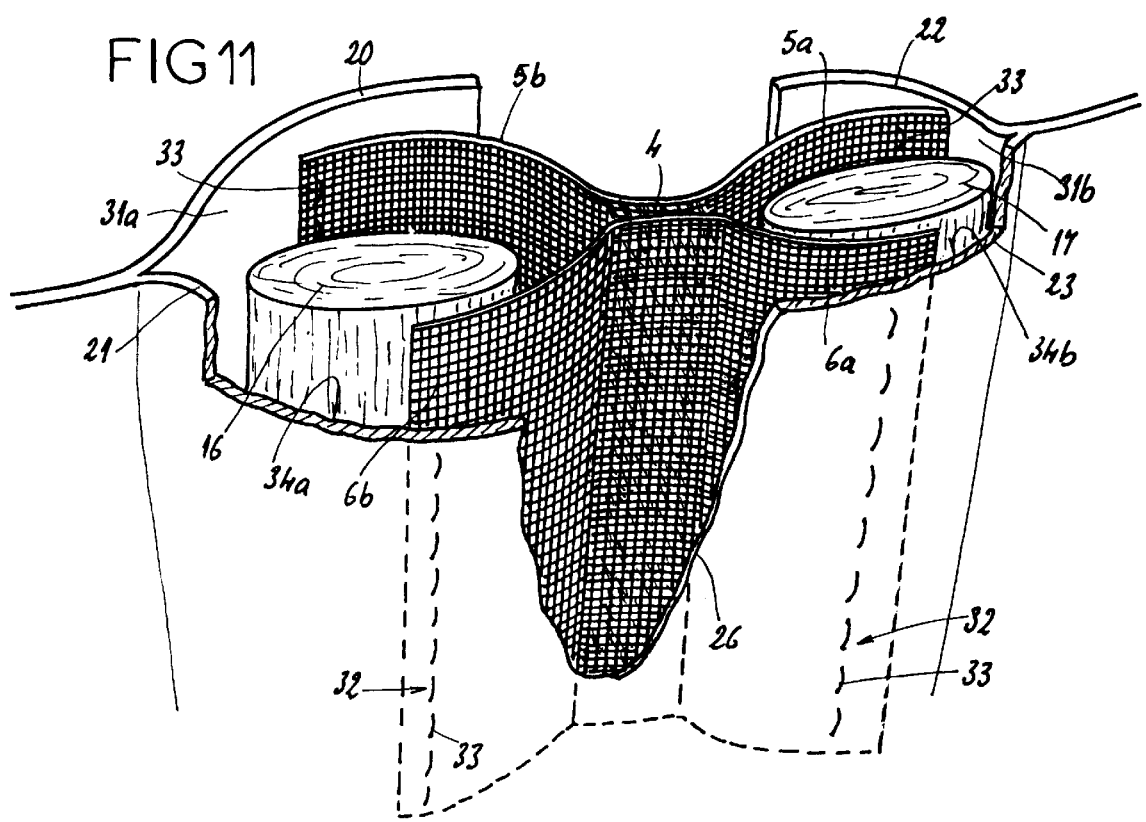
FIG. 11 is a partially cut away close-up view of FIG. 9 and shows an example of application of the preferred prosthetic device illustrated in FIG. 1 for repairing a vertical eventration.

The prosthetic device according to FIG. 1 is positioned as shown in close-up in FIG. 11, and as detailed hereafter.

In a non-obligatory first step, the sheets (2, 3) of the prosthetic device are cut by the surgeon to match the size of the tear (26) formed by the eventration, both in length and in width. The three-dimensionally structured joining strip (4) may in addition, be cut away between the sheets at an edge, so that the flaps (5a, 5b, 6a, 6b) may be separated at these points. However, this last step is not obligatory, and the three-dimensionally. structured strip (4) of the prosthetic device (1) can simply be attached to the inferior part of the tear (26) via sutures or other appropriate means (not illustrated), for example by staples. If the edges are cut into as mentioned above, it is moreover possible to attach the prosthetic device (1) more securely.

Generally when carrying out the repair, the aim is to attach two posterior flaps (5a, 5b) to the interior of the abdomen, while ensuring that no open area remains which could possibly entrap an intestinal loop (28).

The next step involves attaching a first posterior flap (5a), as far in as possible, i.e. as near to the sides of the body as possible, to either the interior surface of the peritoneum (27) or the abdominal wall, or on the outer surface (31a) of the posterior sheath (20) of a first rectus muscle, along the edge zone (32) of the flap (5a). The first two options are not illustrated in the drawings, and the third option, as represented by FIG. 11, is preferred for the reasons given below. The attachment can be carried out either with suture threads or staples (33), for example using an automatic stapler and is typical of the technique used for attaching simple prosthetic devices, i.e. prostheses comprising only one sheet or flap. If the posterior flap (5a) is attached to the interior surface of the peritoneum (27), it can be attached in such a way that the attached edge zone (32) folds back down onto the surface of the remainder of the flap (5a) due to the pressure exerted on it from the overlying peritoneum (27) and abdominal wall. In other words, the posterior flap (5a) is attached so that a portion of its underside or lower surface is in contact with the interior surface of either the peritoneum (27) or the abdominal wall. The procedure is repeated for the second posterior flap (5b), preferably at the same distance from the site of eventration.

As stated above, the posterior flaps (5a, 5b) may be attached either to the interior surface of the peritoneum (27) or the abdominal wall, or on the outer surfaces (31a, 31b) of the posterior sheaths (20, 22) of the rectus muscles. The second alternative is preferentially chosen in order to avoid the risk of complications arising from the prosthesis sticking to the intestines and creating bridges which can lead to occlusion, but the technique involved is itself very intricate and extremely difficult to perform. The third choice, and the one represented by FIG. 7, i.e. attaching the posterior flaps (5a, 5b) to the outer surfaces (31a, 31b) of the posterior sheaths (20, 22) of the rectus muscles (16, 17) is easier to perform and avoids the problems mentioned above. However, the final choice of position depends on the surgeon carrying out the operation and the particular anatomy of the patient concerned.

The anterior flaps (6a, 6b) remain free during this period of the operation, and are attached subsequently to the internal surfaces (34a, 34b) of the anterior sheaths (21, 23) of the rectus abdominis muscles (16, 17). This protects the prosthetic device (1) from contact with the exterior, since the rectus abdominis muscles (16, 17), at the site (26) of eventration are only covered by relatively weak layers of subcutaneous (29) and cutaneous (30) tissue. The aim is therefore to maximise the protective cover over the anterior flaps (6a, 6b) by using the aponeurosis, i.e. the anterior sheaths (21, 23) of the rectus muscles (16, 17), so that no contact with the exterior via the cutaneous wound is possible.

FIG. 12 essentially illustrates more schematically the view of FIG. 11, with the addition of a suture closure (37) for the layer of cutaneous tissue (30) to prevent infection.

In an alternative method, and as illustrated by FIGS. 5 and 7, the prosthetic device (1) may be fastened directly onto the rectus muscles (16, 17) using sutures or staples (33) to attach flaps (6a, 6b), which will protect the adjacent areas at the same time. The staples can be inserted by peritoneoscopy. In another alternative method sutures or staples (33) can also be fastened along the edge of the three-dimensionally structured joining strip and themselves be attached to and interconnected by an annular thread (36), threaded through said joining strip (4), the sutures or clips (33) interacting directly with the muscles (16, 17) or aponeuroses, and being covered by the flaps (6a, 6b).

The prosthetic unit as defined can be sterilized, for example by gamma rays, and can be made in various dimensions.

It will be understood from the foregoing that the three-dimensionally structured joining strip (4) can serve to replace the linea alba (19), when the prosthetic device is in place. The pushing forces, movements or thrust generated by the internal organs such as the intestines are absorbed by the resistant threedimensional structure, which redirects or resolves the forces to the flaps (5a, 5b, 6a, 6b) attached preferably to the posterior (20, 22) and anterior (21, 23) sheaths. The distributed forces are thus reduced and the prosthetic device does not cause the sutures or staples to detach, which in turn prevents recurrence of the eventration. Additionally, the prosthetic fabric material used for the sheets (2, 3) and strip (4) is sufficiently flexible to permit the patient to have substantially normal abdominal muscle movement.

What is claimed is:

1. A prosthetic device for repairing an incisional hernia resulting from a tear in a linea alba between a first and second muscles, each muscle having an anterior and a posterior faces, and being protected by a sheath; and from a pushing pressure or thrust of internal organs or part thereof into an anatomic space created by said tear, said device comprising a monolithic element consisting of:

a three dimensional structure consisting of a first and a second substantially planar strips of a colonisable flexible fabric material, extending substantially parallel to each other and linked by a plurality of filaments or fibers forming a substantially void joining element:

a first and second pair of flaps, each flap extending from a respective opposing lateral edge of a respective one of said first and second strips, and being of the same colonisable flexible fabric material, wherein said first and second substantially planar strips, said first and second pair of flaps and said substantial void joining element are formed integrally in a knitting or weaving process; and where in said three-dimensional structure is positioned in said anatomic space without plugging it and said flaps are positioned and attached so as to form an x-shaped profile surrounding said first and second muscles, and so as to substantially recreate the linea alba such that said three dimensional structure thus positioned resolves forces generated by said pushing pressure or thrust and prevents recurrence of the incisional hernia.

2. A prosthetic device according to claim 1, wherein the joining element has a thickness comprised between about 0.7 mm to about 6 mm.

3. A prosthetic device according to claim 1, wherein the joining strip is from between about 10 cm to about 70 cm in length.

4. A prosthetic device according to claim 1, wherein the planar strips are made from fray resistant fibers or filaments.

5. A prosthetic device according to claim 1, wherein the planar strips are made from fray resistant knitted polyester fibers.

6. A prosthetic device according to claim 1, wherein the device is impregnated with collagen, to favor penetration of connective tissue cells for improved integration.

7. A prosthetic device according to claim 1, wherein the joining element is formed by knitting weft filaments from said first planar strip with weft filaments from said second planar strip.

8. A prosthetic device for repairing an incisional hernia resulting from a tear in a linea alba between a first and a second muscles, each muscle having an anterior and a posterior faces, and being protected by a sheath; and from a pushing pressure or thrust of internal organs or part thereof into an anatomic space created by said tear, said device comprising a monolithic element consisting of:

a three dimensional structure consisting of a first and a second substantially planar strips of a colonisable flexible fabric material, extending substantially parallel to each other and linked by a plurality of filaments or fibers forming a substantially void joining element;

a first and a second pair or flaps, each flap extending from a respective opposing lateral edge of a respective one of said first and second strips, and being of the same colonisable flexible fabric material, wherein said first and second substantially planar strips, said first and second pair of flaps and said substantial void joining element are formed integrally in a knitting or weaving process; and wherein said three-dimensional structure is positioned in said anatomic space without plugging it and said flaps are positioned and attached so as to form an x-shaped profile surrounding said first and second muscles, and so as to substantially recreate the linea alba such that said three dimensional structure thus positioned resolves forces generated by said pushing pressure or thrust and prevents recurrence of the incisional hernia, said prosthetic device further comprising an annular thread threaded through said strip, and having suture clips attached to said thread.

9. A method of repairing an incisional hernia, resulting from a tear in or a collapse of a linea alba linking a first and second muscles said first and second muscles being the left and right rectus abdomens muscles and having an anterior and posterior faces, and from a pushing movement or thrust of an internal organ into an anatomic space created by said tear or collapse, comprises the following steps:

applying to the incisional hernia a prosthetic device comprising a three-dimensionally structured joining strip including filaments, said joining strip occupying a volume of space including defined by said filaments and empty space wherein the portion of the volume comprising the filaments is substantially less than the portion of the volume comprising empty space, a first and second substantially planar sheets of a colonisable flexible prosthetic fabric material extending substantially parallel to each other, and linked together by said joining strip, thus forming two opposite faces respectively common to said first and second planar sheets, each of said planar sheets comprising flap extensions lying opposite to each other on either side of an edge part of a corresponding face of said joining strip, placing and attaching the flaps of said first substantially planar sheet of said prosthetic device in proximity to the posterior face of the two muscles, placing the joining strip of said prosthetic device in a position formerly occupied by the torn linea alba in the anatomic space, placing and attaching the flaps of said second substantially planar sheet of said prosthetic device in proximity to the anterior face of said muscles, such that the joining strip resolves thrust or forces generated by said pushing movement in a position formerly occupied by the torn linea alba in the anatomic space to dissipate said forces and to transfer said forces to said first and second planar sheets.

10. A method according to claim 9, wherein the device is preshaped to a size corresponding to the incisional herin to be repaired before application.

11. A method according to claim 9, wherein the device is preshaped by cutting the sheets of the device to the required size and separating, by cutting away, a part of said joining strip at edges of said sheets.

12. A method according to claim 9, wherein the joining strip of the prosthetic device is attached directly to a same face of the two muscles by suture clips which are themselves attached and interconnected by an annular thread threaded through said strip.

* * * * *